United States Patent
Kara et al.

(10) Patent No.: US 8,412,304 B2
(45) Date of Patent: Apr. 2, 2013

(54) SEALING OF AN IMPLANTABLE MEDICAL DEVICE

(75) Inventors: Sule Kara, Coogee (AU); Martin Svehla, Botany (AU); Edmond Capcelea, Sydney (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 12/830,036

(22) Filed: Jul. 2, 2010

(65) Prior Publication Data
US 2011/0015686 A1    Jan. 20, 2011

(51) Int. Cl.
*A61B 5/04* (2006.01)
*A61N 1/00* (2006.01)

(52) U.S. Cl. .............. 600/395; 607/2; 607/38; 607/116; 430/320

(58) Field of Classification Search ............... 607/2, 36, 607/116; 600/395; 430/320
See application file for complete search history.

(56) References Cited

U.S. PATENT DOCUMENTS

| 4,940,858 | A | 7/1990 | Taylor et al. |
| 6,844,023 | B2 | 1/2005 | Schulman et al. |
| 2003/0087197 | A1 | 5/2003 | Schulman et al. |
| 2006/0105275 | A1 * | 5/2006 | Maloney et al. ............. 430/320 |

* cited by examiner

*Primary Examiner* — Nicole F Lavert
(74) *Attorney, Agent, or Firm* — Kilpatrick, Townsend & Stockton, LLP.

(57) ABSTRACT

A method of adhering a protective layer applied to a substrate region of an implantable medical device (IMD) to form a covered substrate region. The method includes obtaining the IMD, depositing an intermediate layer on a portion of the substrate region of the IMD such that the intermediate layer binds to the portion of the substrate region to create a modified substrate region, and depositing the protective layer after depositing the intermediate layer onto the intermediate layer and adhering the protective layer to the intermediate layer. In an embodiment of the present invention, this method enhances the sealing characteristics of the protective layer by, for example, reducing the likelihood of delamination of the protective layer from the IMD relative to IMDs prepared by certain other methods.

20 Claims, 10 Drawing Sheets

SEALING OF AN IMPLANTABLE MEDICAL DEVICE

CROSS-REFERENCE TO RELATED APPLICATIONS

This Patent Application claims foreign priority to Australian Patent Application No. 2009903327, entitled "Sealing of an Implantable Medical Device," filed on Jul. 16, 2009 (lapsed), the content of which is hereby incorporated by reference herein.

BACKGROUND

1. Field of the Invention

The present invention generally relates to implantable medical devices, and in particular, to the sealing of an implantable medical device for use within a human body.

2. Related Art

Implantable medical devices (IMDs), such as cochlear implant components, are commonly comprised of delicate mechanical and electrical components and upon implantation into a human body are typically subjected to long term exposure to relatively harsh environmental conditions due to, for example, the presence of conductive body fluids. As such, protection is often provided of the implanted device from the surrounding body environment to reduce the risk of failure of the implanted device and also to reduce the potential for leakage of any non biocompatible material from the implanted device into the body of the recipient.

Often, a combination of various sealing or protective methodologies is employed with IMDs. By way of example only, FIGS. 1 and 2 present an implantable receiver/stimulator 124 which corresponds to the implanted part of an exemplary cochlear implant system as known in the art. Receiver/stimulator 124 includes a receiver unit 132 and a stimulator unit 120. Receiver unit 132 is generally circularly shaped and incorporates a peripherally located internal antenna coil 133 having a centrally located attachment magnet 21 received within a pocket 22. Stimulator unit 120 incorporates the processing electronics which are non biocompatible for processing the signal received from receiver unit 132 and an extra-cochlear electrode (ECE) plate 129.

Extending from stimulator unit 120 is a first electrode lead 140 terminating in an electrode assembly 144 having a plurality of individual electrodes 142 and a second reference electrode lead 147 terminating in a reference ECE ball 148 comprising a rigid ball formed of platinum. Reference ECE ball 148 and ECE plate 129 both provide a return pathway for current applied at the electrodes 142 of electrode assembly 144 in the commonly used stimulation mode.

In order to provide an initial hermetic protective layer so that the various non biocompatible elements of the IMD are isolated from the environment upon implantation into a human body, the non biocompatible elements such as the processing electronics of the stimulator unit 120 are housed within an outer rigid shell or housing 121 formed of a biocompatible material such as platinum, titanium or palladium. Often, any component that is attached to an opening in housing 121 such as the ECE plate 129 is hermetically welded to the housing 121 in order to maintain the hermetic seal.

Another complication in hermetically sealing non biocompatible elements within an outer rigid shell or housing in an IMD such as the cochlear implant system depicted in FIGS. 1 and 2 is where a biocompatible component such as a wire formed of platinum is connected at one end to one or more of the non biocompatible elements of an IMD, such as electronic circuitry, and further to have a second end or region that is exposed to the body environment such as to convey or receive an electrical signal. Achieving this functionality requires a "feedthrough" region through which the component extends and which functions as a hermetic protective layer to separate the non biocompatible region of the IMD from the biocompatible region.

Again with reference to the illustrative example of the receiver/stimulator 124 depicted in FIGS. 1 and 2, there is shown in FIG. 3 the feedthrough region 300 which is located under the cap 11 (which is not hermetically sealed to housing 121) located on the underside of the stimulator unit 120 as illustrated in FIG. 2. Each of the 22 electrode wires 330 which form together electrode lead 140 and which terminate to form individual electrodes 142 of electrode assembly 144 are connected to individual platinum electrical contacts or pins 320 which at their other end are connected to the processor electronics contained within the housing 121 of stimulator unit 120.

In order to hermetically seal electrical contacts 320, feedthrough region 300 is filled with ceramic material 310 by a powder injection moulding or sintering process which functions to form a hermetically sealing protective layer or barrier, thereby preventing the ingress of body fluids to the non biocompatible regions of stimulator unit 120 or leakage of non biocompatible material to the body environment.

Another secondary level of sealing or a protective layer may be provided for an IMD by encasing or encapsulating the IMD within a flexible biocompatible layer. Encapsulating the IMD within such a protective layer can also provide other benefits such as improved handling due to the increased conformability and lubricity of the resultant encapsulated IMD.

In some instances, the outer surface of the encapsulating material may provide a surface finish less susceptible to the formation of a biofilm. Referring once again to FIGS. 1 and 2, in the case of a cochlear implant system, the receiver/stimulator body 124, electrode lead 140 and the reference electrode lead 147 are encapsulated within a protective layer of polymer such as polydimethylsiloxane (PDMS) or other type of silicone rubber to form a silicone shell 180 leaving electrically active regions such as the electrodes 142 of the electrode assembly 144, the reference ECE ball 148 and the ECE plate 129 exposed. These electrically active regions are typically formed of titanium given this material's combination of excellent electrical properties and biocompatibility.

Referring now to FIG. 4, there is shown a figurative sectional view of the flexible biocompatible protective layer 230 that would typically be applied to a cochlear implant system. A first layer of silicone adhesive 220 is applied to a substrate region 200 (corresponding to a surface of the IMD, for example), to form a covered substrate region 210 to facilitate the attachment of the protective layer 230 of silicone rubber, as generally silicone rubbers will not stick to metal surfaces without an adhesive layer. Silicone adhesive 220 is typically applied manually using a hand gun, although other automated processes may be used. Silicone rubber protective layer 230, which as referred to previously may be a PDMS material or other types of silicone rubber, is typically applied by an injection moulding process to form silicone shell 180. Other materials such as an insulating parylene coating or an initial primer layer may also be used depending on the nature of the substrate region 200. As depicted in FIG. 4, where there is an exposed or uncovered substrate region 215, a boundary region 250 exists between the covered substrate region 210 and any exposed substrate region 215.

Silicone shell 180 typically does not form a hermetic seal, as the silicone rubber material has some liquid permeability, but rather functions as a secondary protective layer to the hermetic sealing provided by the housing 121 and the feedthrough region 300. Still, this secondary protective layer aids in preventing the ingress of body fluids into the IMD or the leakage of non biocompatible materials from the IMD.

While generally these sealing methodologies are very effective, they can be improved. In the case of a cochlear implant, the seal durability is especially important due to the extended time that the implant is expected to remain in the body of the recipient (i.e., for periods of greater than 75 years). Seal durability is also important when the substrate or surface to which the protective layer is applied to includes an electrically active surface portion of the IMD (i.e., a surface portion that during operation of the IMD will conduct current often in a rapidly varying manner).

SUMMARY

According to an embodiment of the present invention, there is a method of adhering a protective layer applied to a substrate region of an implantable medical device (IMD) to form a covered substrate region. The method comprises obtaining the IMD, depositing an intermediate layer on a portion of the substrate region of the IMD such that the intermediate layer binds to the portion of the substrate region to create a modified substrate region, and depositing the protective layer after depositing the intermediate layer onto the intermediate layer and adhering the protective layer to the intermediate layer. In an embodiment of the present invention, this method enhances the sealing characteristics of the protective layer by, for example, reducing the likelihood of delamination of the protective layer from the IMD relative to IMDs prepared by certain other methods.

According to another embodiment of the present invention, there is an implantable medical device (IMD), comprising a housing assembly containing electronics components, the housing assembly including a substrate region, an intermediate layer adhering to the substrate region, and a protective layer adhering to at least the intermediate layer. In an embodiment of the present invention, the intermediate layer enhances the sealing characteristics of the protective layer by, for example, reducing the likelihood of delamination of the protective layer from the IMD relative to IMDs that do not include the intermediate layer.

BRIEF DESCRIPTION OF THE DRAWINGS

Embodiments of the present invention will be discussed with reference to the accompanying drawings wherein.

DETAILED DESCRIPTION

Figure 5:
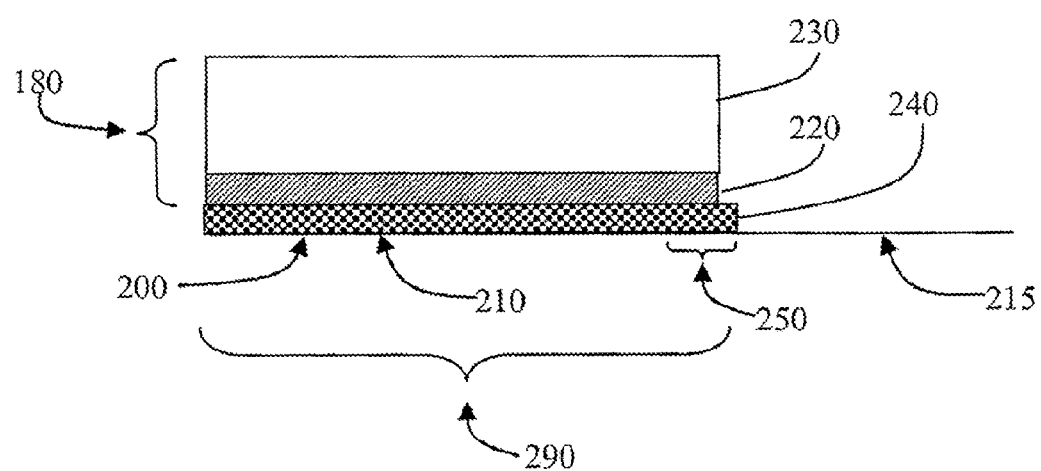
FIG. 5 presents a schematic illustrating a sectional view of a flexible protective layer applied to a substrate region as illustrated in FIG. 4, having a protective layer that is enhanced in accordance with a first illustrative embodiment of the present invention.

In the following description, like reference characters designate like or corresponding parts throughout the various drawings. With reference to FIG. 5, there is shown a schematic depicting a cross-sectional view of a protective layer 230 applied to a substrate region 200 of an implantable medical device, such as a stimulator of a cochlear implant, forming a covered substrate region 210 according to a first illustrative embodiment of the present invention. In this illustrative embodiment, the substrate region 200 comprising the exposed substrate region 215 and the covered substrate region 210 is formed of platinum. While platinum is a particularly suitable biocompatible material for implantable medical devices, and in particular for electrically active regions of such devices, platinum includes a mobile oxide layer. The present inventor has recognized that the oxide layer which forms on the substrate region 200 increases the susceptibility of the silicone shell 180, and hence the protective layer 230, to delamination at the boundary region 250 and further at the covered substrate region 210, thereby resulting in the protective layer 230 of silicone shell 180 being compromised.

The present inventor has determined that the weakening of the bond of the protective layer 230 at the regions just identified is increased when the substrate region 200 is electrically active and in the presence of ionic fluids such as body fluids. Although this delamination is not a failure mode, an embodiment of the present invention is directed towards limiting delamination. In an exemplary embodiment, the sealing characteristics of the protective layer 230 may be improved/enhanced.

In accordance with an embodiment of the present invention, as shown in FIG. 5, an intermediate layer 240 of titanium is deposited by a sputtering process onto a portion of the substrate region 200 to form a modified substrate region 290 comprising, in this illustrative embodiment, the covered substrate region 210 and boundary region 250. As intermediate layer 240 of deposited titanium includes a stable oxide component, modified substrate region 290 provides an increased adhesion affinity between the bound intermediate layer 240 and the protective layer 230, as compared to the adhesion affinity of the original covered substrate region 210 with protective layer 230. In an embodiment, this may improve the sealing characteristics of the protective layer 230 with respect to the covered substrate region 210.

In an embodiment, the adhesion affinity is enhanced by increasing the surface energy of the modified substrate region as compared to the original substrate region. In another embodiment, the adhesion affinity is enhanced by increasing the stability of the chemical bond between the modified substrate region and the protective layer as compared to the original substrate region.

With respect to the illustrative embodiment of FIG. 5, in an exemplary embodiment, the increased adhesion affinity is due to the lower surface tension or energy between the intermediate layer 240 of sputtered titanium and the protective layer 230 formed of silicone rubber as compared to the original platinum silicon bond between the covered substrate region 210 and the protective layer 230. Platinum, similar to most plastics, has a surface tension or energy below 50 dynes/cm and is more difficult to adhere to compared with titanium whose surface tension or energy is approximately 250 dynes/cm. In addition, the overall adhesion affinity is increased as the bond between the intermediate layer 240 of titanium and the protective layer 230, i.e. the Ti—O—Si bond, is more stable compared to the bond between the original covered substrate region 210 of platinum and protective layer 230, i.e. the Pt—O—Si bond, further increasing or enhancing the overall resultant adhesion between modified substrate region 290 and protective layer 230.

Accordingly, in an exemplary embodiment, the increased surface tension/energy of sputtered titanium relative to platinum will increase the "wettability" of the surface and hence the adhesion affinity of the surface. In addition, the stability of the titanium oxide formed by the sputtering process on substrate region 210 will improve the durability of adhesion.

Intermediate layer 240 of titanium may be deposited on the substrate region 200 through vapor deposition. An exemplary embodiment includes, as a method of vapor deposition, sputter deposition involving the removal of atomized material from a solid target due to energetic bombardment of its surface layers by ions or neutral particles. These particles are then deposited onto the substrate. If selective areas need to be coated, substrates can be masked to cover portions that are not intended to be coated. As would be appreciated by those skilled in the art, other types of deposition processes not necessarily limited to physical or chemical vapor deposition are contemplated within the scope of the invention.

Figure 6A:
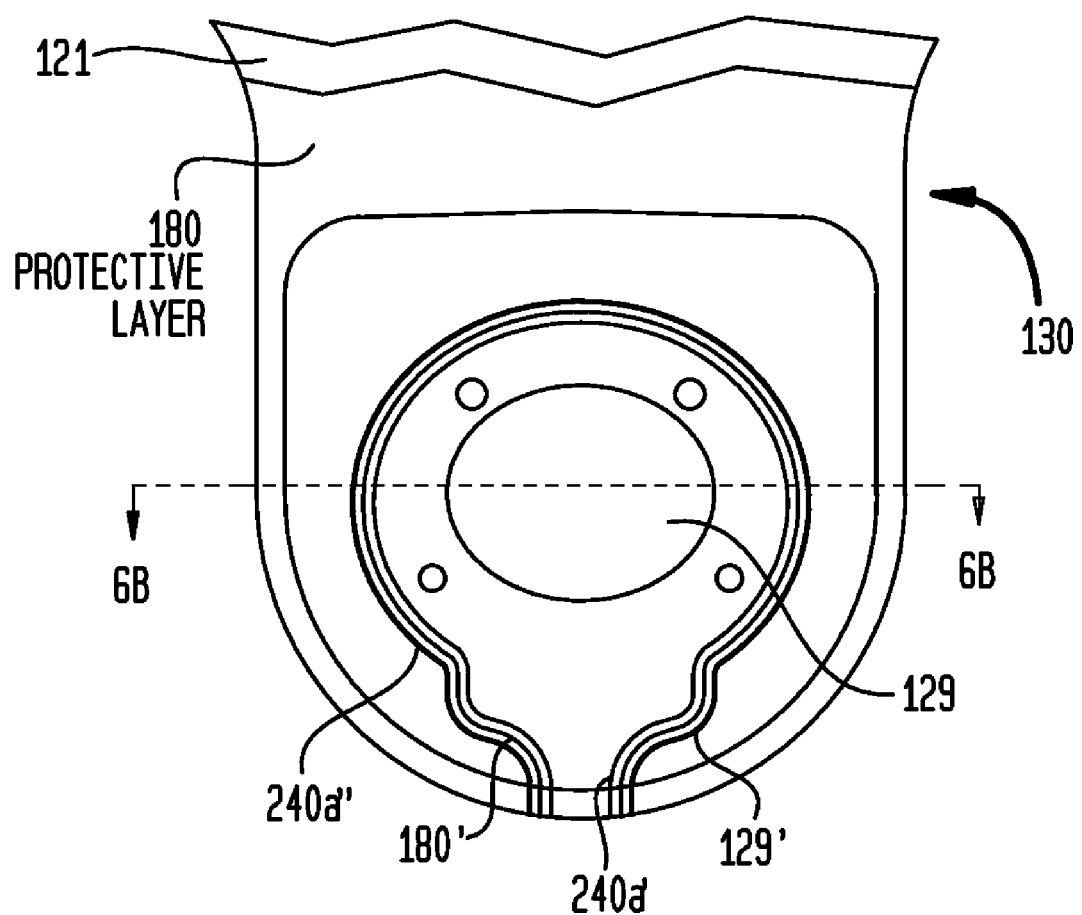
FIG. 6A presets a schematic illustrating a front view of the stimulator of the cochlear implant system illustrated in FIG. 1 including a first example substrate region having a protective layer according to an embodiment of the present invention.
Figure 6B:
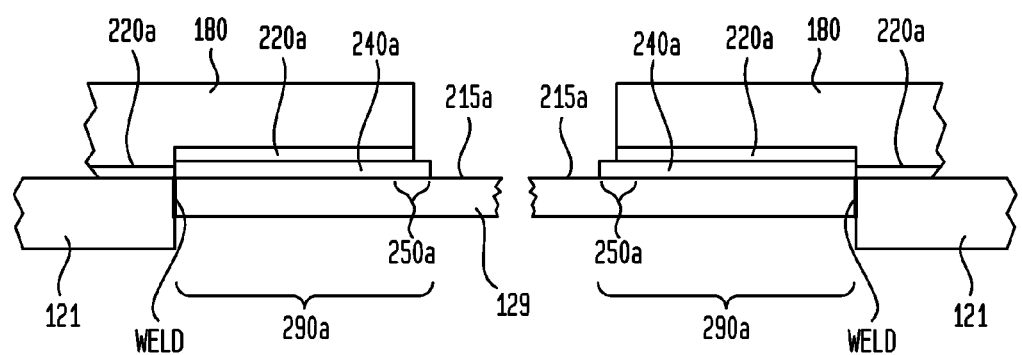
FIG. 6B depicts a cross-sectional view through the stimulator of the cochlear implant depicted in FIG. 6A.
Figure 7:
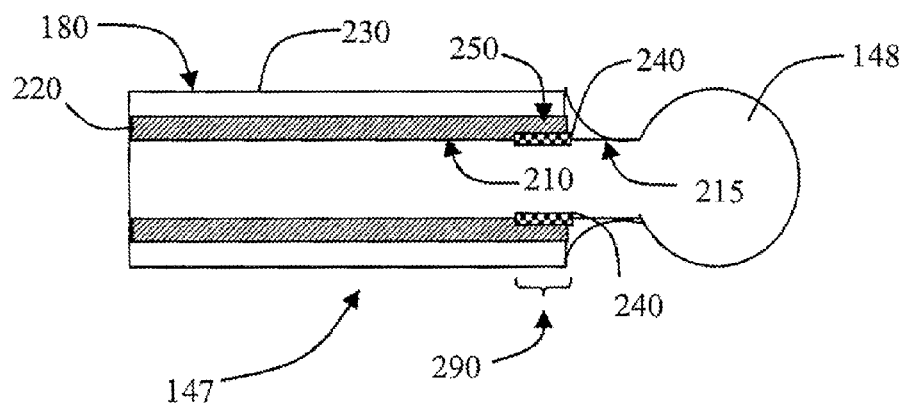
FIG. 7 depicts a side sectional view of the reference electrode lead and reference ECE ball of the cochlear implant system illustrated in FIG. 1 with a second example substrate region having a protective layer according to an embodiment of the present invention.
Figure 8:
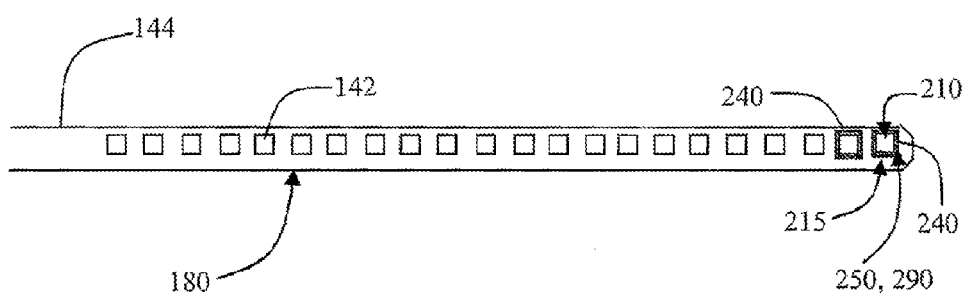
FIG. 8 depicts a side sectional view of the electrode assembly of the cochlear implant system illustrated in FIG. 1 with a third example of a substrate region having a protective layer according to an embodiment of the present invention.

Referring now to FIGS. 6 to 8, there are shown various parts of a cochlear implant system each having substrate regions having a protective layer obtained according to the method and system of the present invention. In these illustrative examples, each of these substrate regions includes electrically active regions formed of platinum. As would be apparent to those skilled in the art, while the present invention is described in relation to various applications to substrate regions of a cochlear implant system it will be appreciated that the invention will be equally applicable to other IMDs.

As shown in FIGS. 6A and 6B (FIG. 6B being a cross-sectional view taken from FIG. 6A), platinum ECE plate 129 which is hermetically welded to titanium housing 121 is an example of a substrate region including a covered substrate region 210a of platinum having a protective layer of silicone rubber 180 corresponding to protective layer 230 of FIG. 5 and an exposed substrate region 215. In accordance with the present invention, an intermediate layer 240a of titanium is sputtered onto a portion of the covered platinum substrate region 210a and the platinum boundary region 250a to form a modified substrate region 290a. In this manner, the sealing characteristics of the protective layer of the silicone rubber 180 are enhanced due to the increased adhesion between the modified substrate region 290a including the intermediate layer 240a of sputtered titanium and the silicone shell 180. As was the case with the embodiment depicted in FIG. 5, an adhesive 220a is applied onto intermediate layer 240a to adhere silicon rubber 180 to the intermediate layer 240a.

As may be seen in FIGS. 6A and 6B, upon application of the protective layer to the substrate region, there is formed an exposed substrate region having no protective layer, thereby defining a boundary region between the covered substrate region and the exposed substrate region.

In the above illustrative example, the surface changes from the platinum portion of the ECE plate 129 to that of the titanium housing 121. Accordingly, it is only necessary to sputter the covered platinum substrate region 210a that is overlayed by the protective layer of silicon rubber 180 to improve the sealing characteristics to resist delamination and not the titanium housing 121 which will already have satisfactory sealing characteristics. However, in practice portions of the titanium housing 121 may also be sputtered with titanium depending on the degree of accuracy in the sputtering process without adversely affecting the performance of the sputtered titanium region.

Thus, referring to FIG. 6A, the intermediate layer 240a has a first boundary 240a' and a second boundary 240a". In the embodiment depicted in FIG. 6A, the intermediate layer 240a extends across boundary 180', which corresponds to the boundary of the protective layer of silicon rubber 180 following the boundary 129' formed between the ECE plate 129 and the housing 121 (the ECE plate 129 and the housing 121 forming a housing assembly 130).

As would be appreciated by those skilled in the art, the degree and extent of the intermediate layer 240a may be varied according to requirements. In this illustrative embodiment, the present invention is applied to provide a modified substrate region 290a in the form of a reinforcing "ring" at the boundary between the covered and exposed portions of the surface of the IMD. Equally, much larger substrate regions may have an intermediate layer 240a applied where appropriate.

Referring to FIG. 7, the covered substrate region 210 located at the end of the reference electrode lead 147 is another suitable substrate region where the present invention may be applied. Electrode lead 147 is formed of platinum and in this example, only the boundary region 250 where the protective layer 230 or silicone shell 180 terminates immediately prior to the ECE ball 148 is sputtered with titanium to form a modified substrate region 290 which is co-located with boundary region 250. In an exemplary embodiment, this improves resistance to delamination at the edge or boundary of the silicone shell 180. In an embodiment, the intermediate layer 240 of sputtered titanium may be deposited further down the reference electrode lead 147 as appropriate. In another illustrative embodiment, the entire reference electrode lead 147 is sputtered with an intermediate later 240 of titanium to improve resistance to delamination down the entire electrode lead 147.

Referring now to FIG. 8, another substrate region 210 that may be modified in accordance with the present invention correspond to the individual electrodes 142 which form the electrode assembly 144 of receiver/stimulator 124. Each individual electrode 142 comprises a platinum pad encased in a protective layer 230 formed by the silicone shell 180, providing an exposed contact region where stimulation current is provided by the cochlear implant system. In this example, the boundary region 250 between the exposed contact substrate region 215 and the covered substrate region 210 is sputtered with an intermediate layer of titanium to form a modified substrate region 290 as depicted with respect to the last two electrodes 142 in FIG. 8.

In an exemplary embodiment, the thickness of the sputtered titanium intermediate layer may range between 0.001 to 10 microns. Depending on the requirements, the thickness of the sputtered layer may extend towards 50 microns in order to obtain the desired adhesion and improvement in sealing characteristics of the flexible protective layer.

An experiment may be performed to evaluate the effectiveness of applying intermediate layer 240 to a platinum substrate region 210 with respect to improving the adhesion of flexible protective layer 230 to substrate region 210. In this experiment, a pair of samples comprising platinum substrate regions each covered with a silicone rubber material are subjected to stress-strain analysis using a peel strength test as outlined in ASTM standard D903 after electrical stimulation in a buffered saline solution. The only substantive difference between the two samples is the presence of an intermediate layer 240 of sputtered titanium applied in accordance with the present invention in the second sample.

Figure 9:
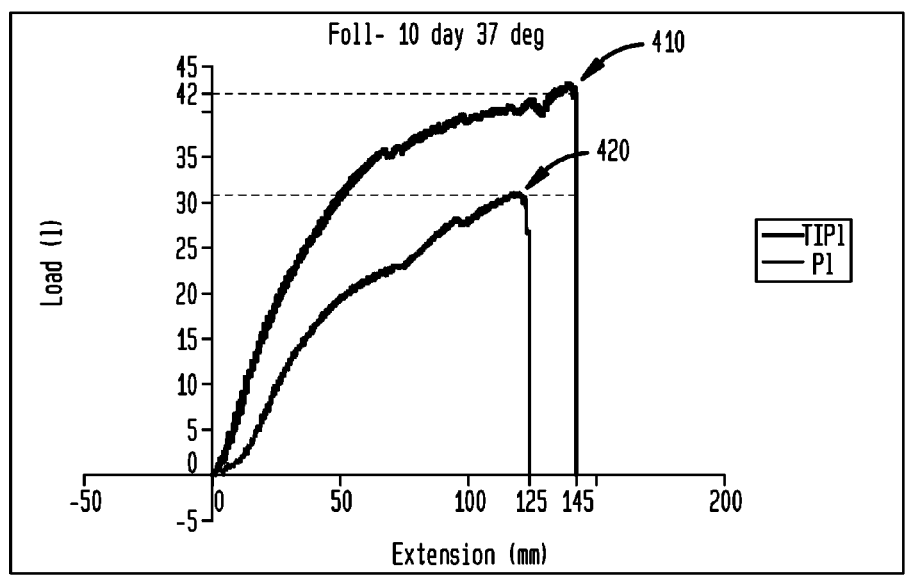
FIG. 9 presents a graph comparing the integrity of adhesion of the protective layer after ten days of electrical stimulation in an ionic solution with respect to the first sample of a protective layer applied to a substrate region and a second sample incorporating a protective layer according to an embodiment of the present invention.
Figure 10:
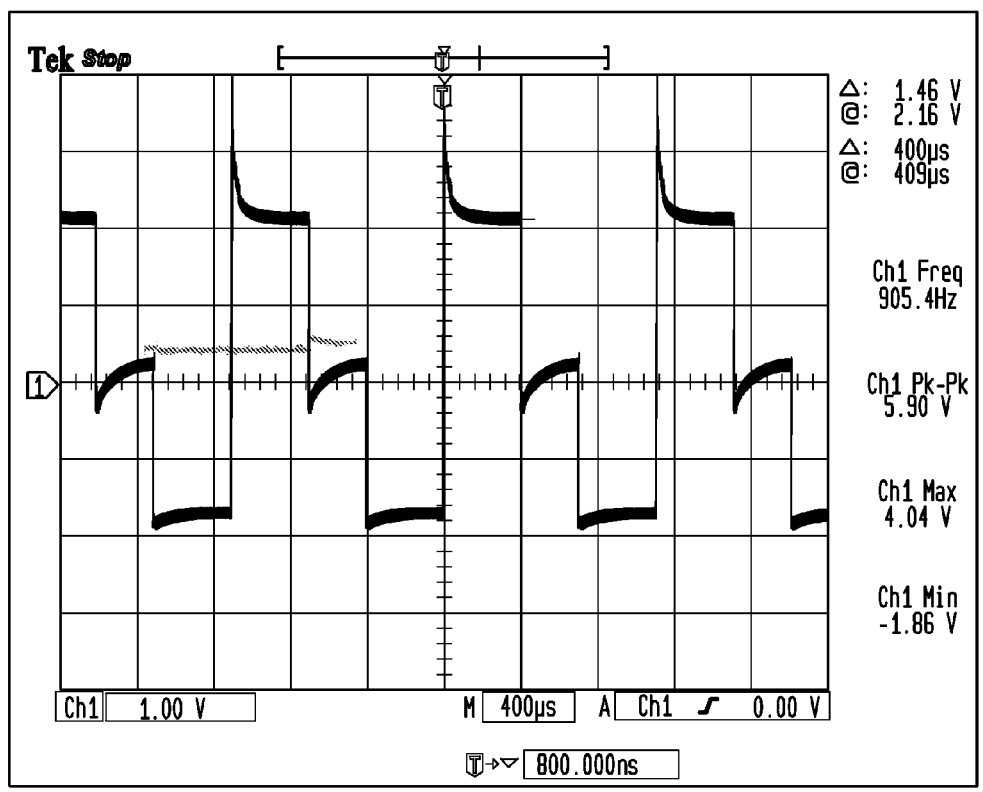
FIG. 10 presents a view as seen from an oscilloscope display, showing the voltage stimulation pattern used to electrically stimulate the samples referred to in FIG. 9.

Referring now to FIG. 9, there is shown a graph of the stress-strain relationship for the pair of samples after being immersed in buffered saline solution and subjected to electrical stimulation for 10 days at 37 degrees Celsius in accordance with the stimulation voltage output displayed in FIG. 10. As can be readily observed, the bond between the modified substrate region 290 and the flexible protective layer 230 in the second sample (corresponding to line 410) is noticeably stronger than the adhesion between the substrate region 210 and the flexible protective layer 230 in the first sample (corresponding to line 420) as the second sample is able to undergo a higher load (stress). As shown by line 410, the second sample (incorporating a sputtered titanium intermediate layer 240) fails at a maximum load of approximately 42 N. In comparison, the first sample fails significantly earlier at a maximum load of approximately 30 N as shown by line 420. As a result, the first sample without sputtered titanium has a 30% lower peel strength under the wet electrically active environment compared to the second sputtered sample, demonstrating the increased adhesion affinity between the sputtered intermediate titanium layer and the sealing material according to an embodiment of the present invention.

With respect to FIG. 9, in both cases, the loss of adhesion between the flexible protective layer 230 formed of silicone rubber and the platinum substrate region 210 underneath may be due to cyclic reduction and/or oxidation reactions at the surface of the stimulating substrate. However, as is apparent from the above results, the loss of adhesion may be more rapid where the metal substrate has a mobile oxide (such as platinum). In an exemplary embodiment, superior adhesion translates into an improved seal at the interface between the polymer and substrate surface, thus providing enhanced sealing characteristics.

As would be apparent to those skilled in the art, the resulting adhesion improvement between the original substrate and the sealing material provides increased protection against the ingress of electrically conductive body fluid through minute pathways in the sealing material to the substrate. As the presence of these body fluids would ordinarily enhance the delamination of the encapsulating sealing material, potentially resulting in the eventual failure of protection provided by the silicone shell 180, some embodiments of the present invention improve the reliability and longevity of the implanted medical device.

While some previous sealing methodologies have attempted to provide a protective layer by sputtering a thin coating of ceramic (without any further sealing material), these methods potentially result in holes forming in the coating during the sputtering process, thereby rendering the insulating and sealing properties of the coating ineffective. In contradistinction to these previous methodologies, the introduction of an intermediate sputtered layer in accordance with the present invention acts in combination with the protective layer to enhance and reinforce the sealing characteristics of the protective layer.

Referring now to Table 1, there is shown a non exhaustive list of the various combinations of substrates and flexible protective layers where an intermediate layer may be applied in accordance with the present invention. As an example, a substrate region of gold covered with a flexible protective layer of polyurethane (PU) may have its sealing characteristics enhanced by sputtering the gold substrate with either ceramic material or titanium.

TABLE 1

| Substrate | Intermediate Layer | Flexible Protective Layer |
|---|---|---|
| platinum, iridium, palladium, gold, ceramic, titanium, carbon nanotube (CNT) | ceramic | Poldimethylsiloxane (PDMS), polytetrafluorethylene (PTFE), polyurethane (PU), polyethersulphone (PES), polyphenylsulphone(PPS), polydimethylsiloxane (PDMS), polyethylene (PE), polyethylene terephthalate |
| platinum, iridium, palladium, gold, ceramic, titanium, carbon nanotube (CNT) | titanium | Poldimethylsiloxane (PDMS), polytetrafluorethylene (PTFE), polyurethane (PU), polyethersulphone (PES), polyphenylsulphone(PPS), polydimethylsiloxane (PDMS), polyethylene (PE), polyethylene terephthalate (PET). |

Figure 1:
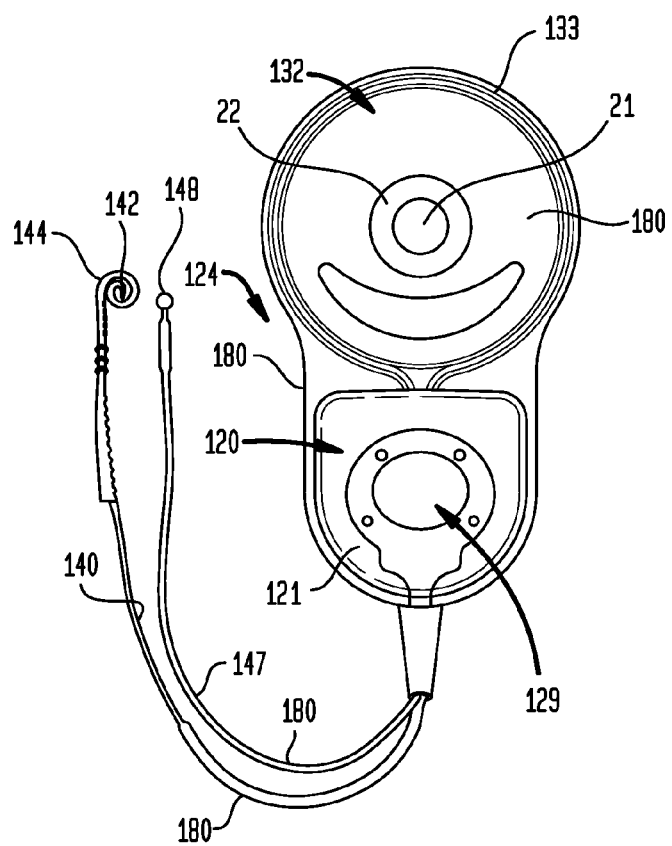
FIG. 1 presents is a front perspective view of a receiver/stimulator of an exemplary cochlear implant system.
Figure 2:
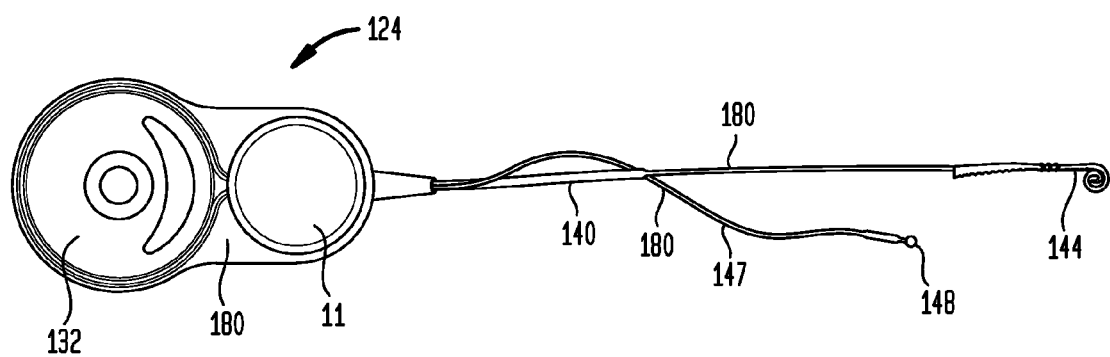
FIG. 2 presents a rear perspective view of the receiver/stimulator illustrated in FIG. 1.
Figure 3:
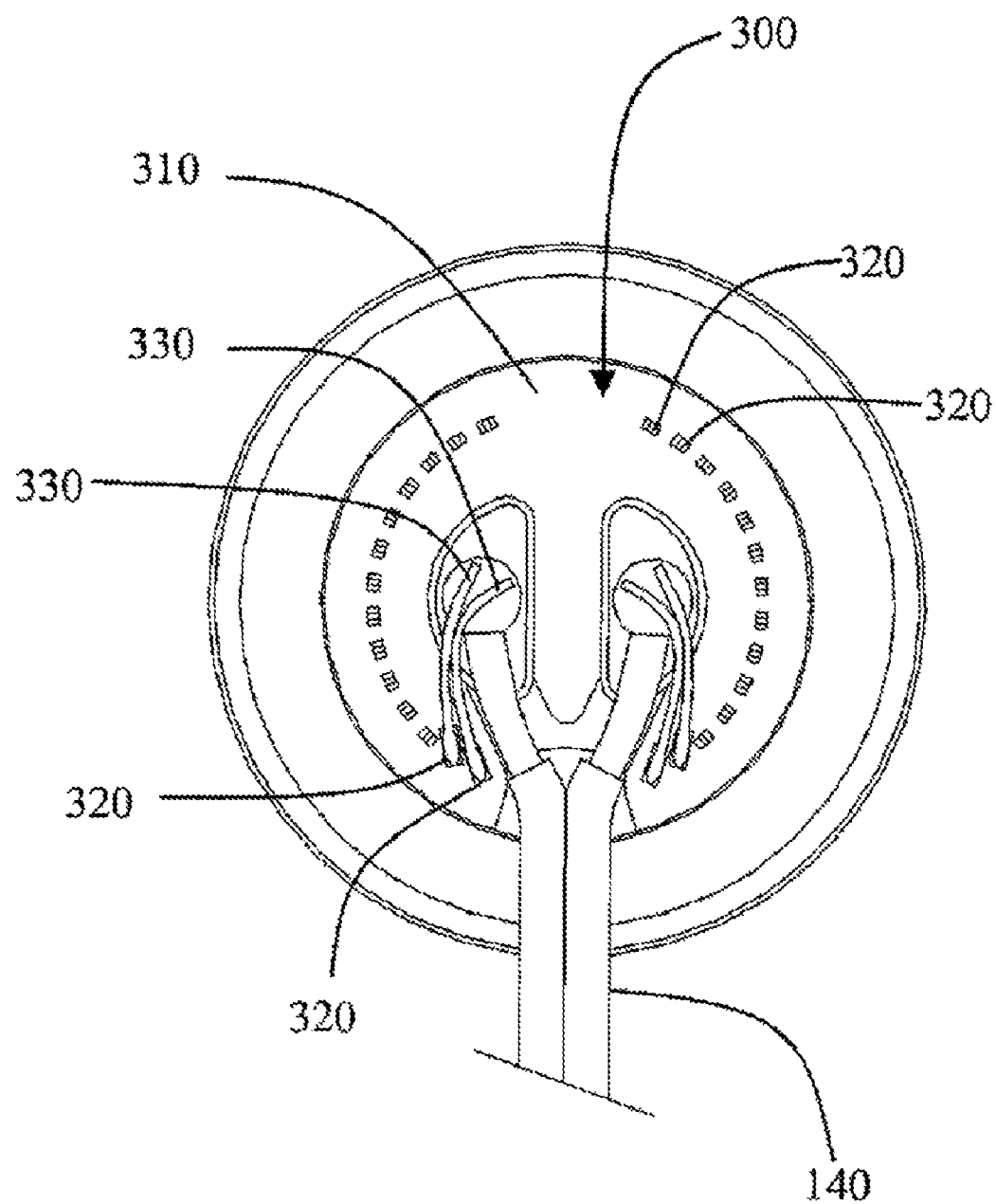
FIG. 3 presents a schematic illustrating the feedthrough region of the receiver/stimulator depicted in FIG. 1.
Figure 4:
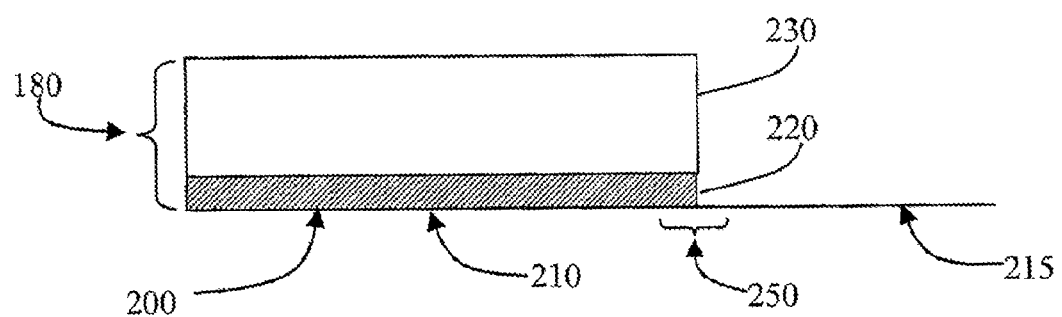
FIG. 4 presents a schematic illustrating a sectional view of a flexible protective layer in the form of a silicone shell as applied to the cochlear implant system illustrated in FIG. 1.
Figure 11:
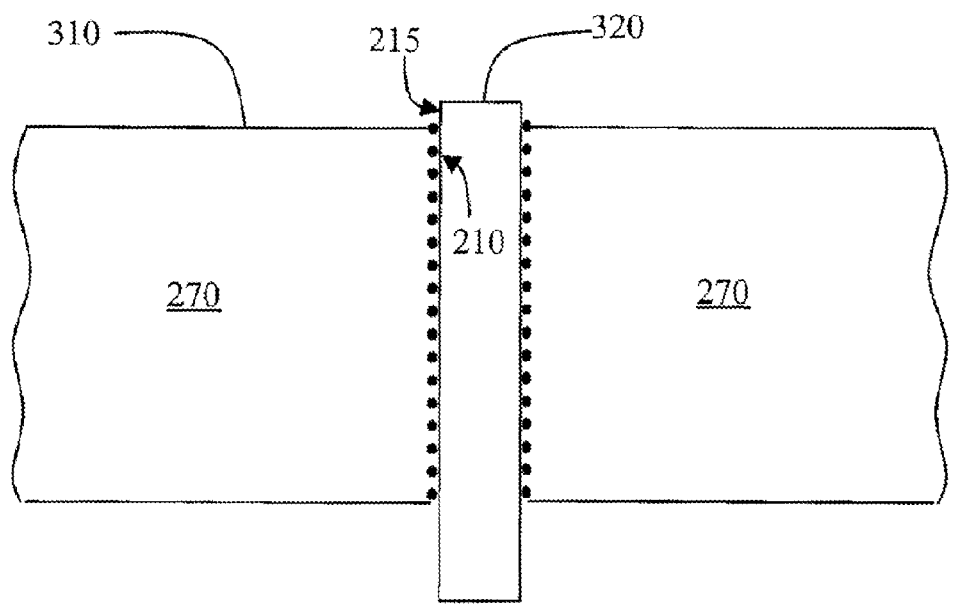
FIG. 11 schematically illustrates a sectional view of the hermetic protective layer of ceramic material as applied to the feedthrough region illustrated in FIG. 3.
Figure 12:
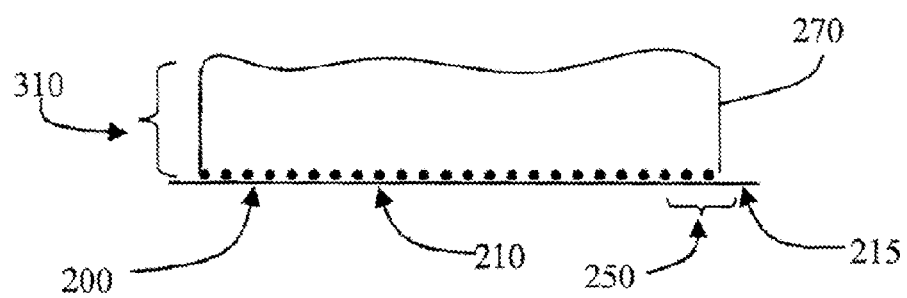
FIG. 12 schematically illustrates a sectional view of the hermetic protective layer of ceramic as illustrated in FIG. 3.

FIG. 11 presents a schematic of a sectional view of a hermetic protective layer 270 in the form of ceramic material 310 as applied to a platinum electrical contact 320 forming a substrate region 210 and an exposed region 215 where the contact is exposed in the feedthrough region 300 of stimulator 120 (with reference to FIG. 3). FIG. 12 presents a view of the same region as depicted FIG. 11 but oriented to be equivalent to the format depicted in FIG. 4. Unlike the flexible protective layer 230 referred to previously, the hermetic protective layer 270 formed by the ceramic powder injection process forms a hermetic seal (as indicated by dotted line) with the covered platinum substrate region 210 in the form of the platinum electrical contact 320. As shown in FIG. 12, there is also a boundary region 250 between the covered substrate region 210 and the exposed substrate region 215.

Figure 13:
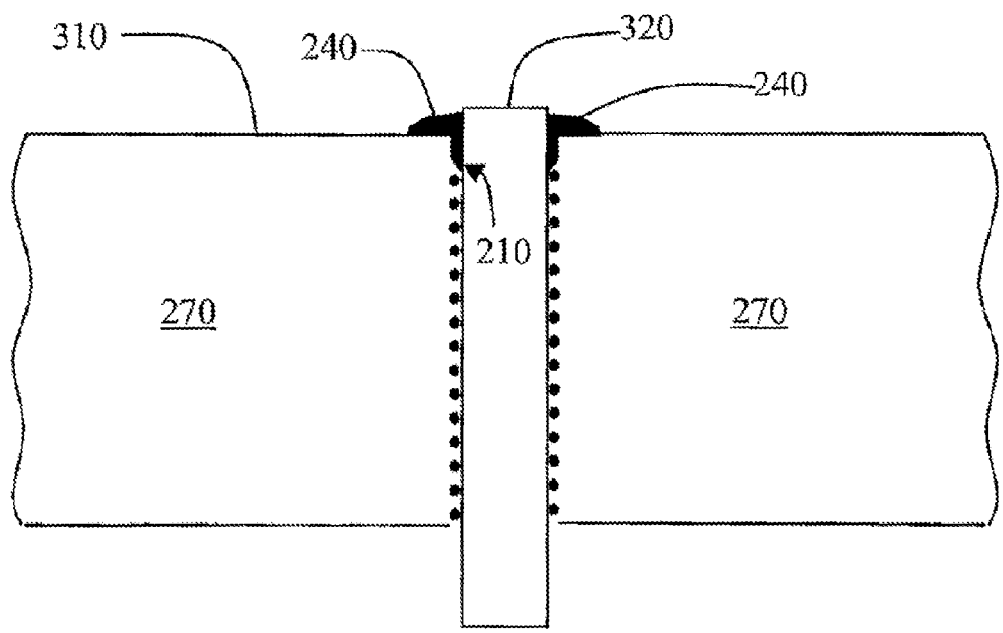
FIG. 13 schematically illustrates a sectional view a protective layer applied to the substrate region as illustrated in FIG. 11 with sealing characteristics according to a second illustrative embodiment of the present invention.
Figure 14:
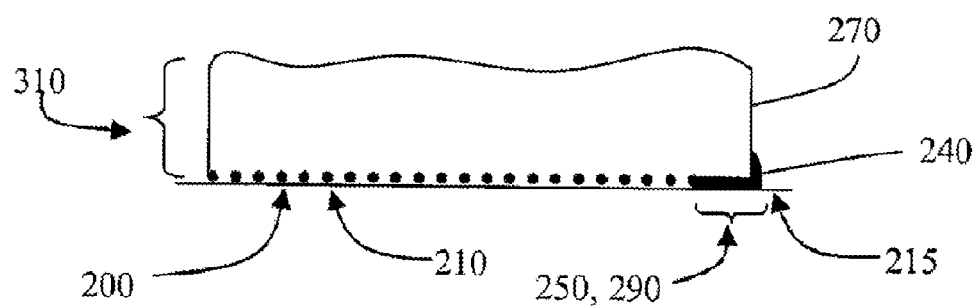
FIG. 14 schematically illustrates a sectional view of a portion of the hermetic protective layer of ceramic as illustrated in FIG. 13.

FIGS. 13 and 14 present schematics of sectional views of the hermetic protective layer 270 of FIGS. 11 and 12 which sealing characteristics that have been enhanced according to a second illustrative embodiment of the present invention where an intermediate layer 240 is deposited on substrate region 210 to form a modified substrate region 290 to improve the interface bonding properties between substrate region 210 and hermetic protective layer 270.

In some instances, the hermetic seal between hermetic protective layer 270 and substrate region 210 may be compromised due to manufacturing processes such as cleaning. By applying an intermediate layer 240 directly by a sputtering process to form a modified substrate region 290 co-located with boundary region 250, defects in the hermetic seal that may result in leaks may be "filled" and the structural integrity of the hermetic seal restored or reinforced. In an embodiment, leaks may be filled in between the substrate region and the protective layer to restore the structural integrity of the hermetic seal. By doing this, in an embodiment, the interface bonding properties may be enhanced/the bond strengthened at the modified substrate region.

Figure 15:
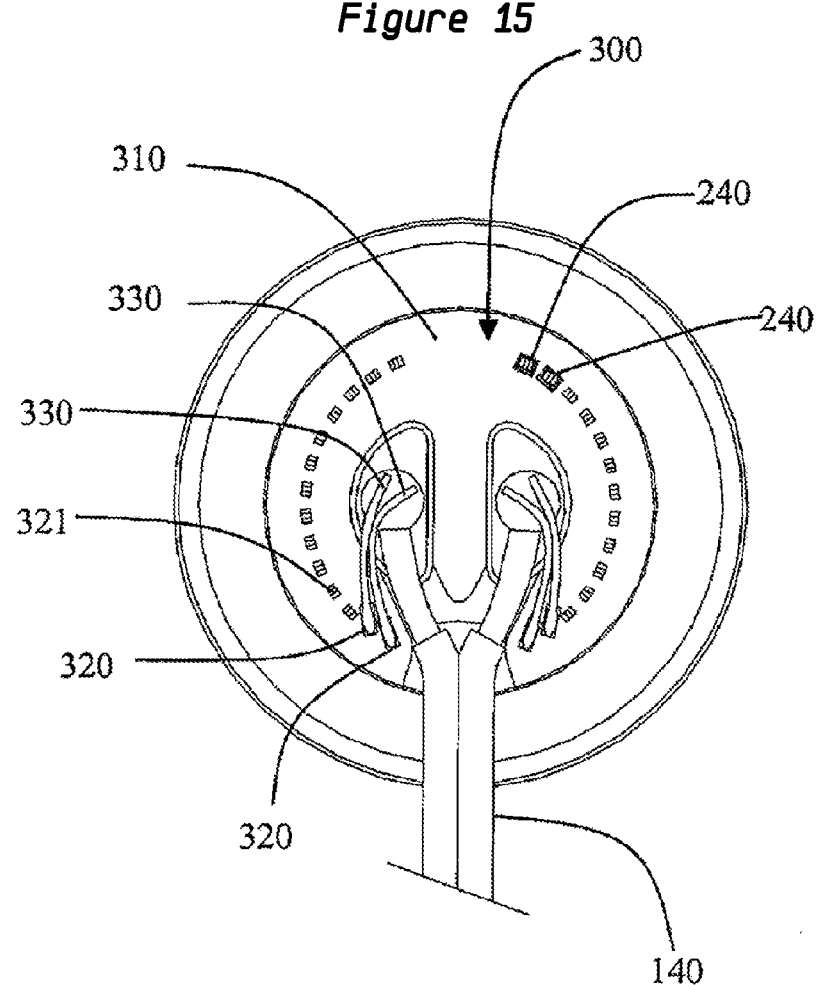
FIG. 15 is a schematic of the feedthrough region of the stimulator illustrated in FIG. 1 depicting a protective layer according to an embodiment of the present invention.
Figure 16:
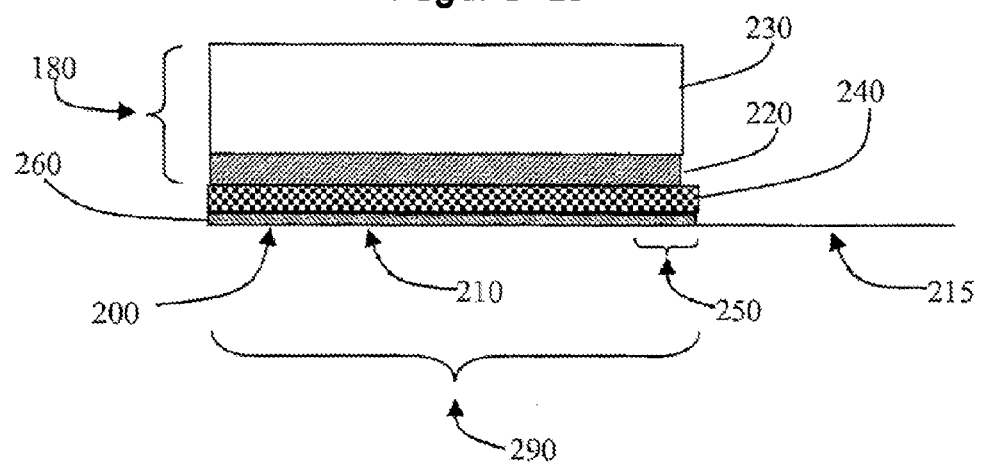
FIG. 16 is a sectional view of a protective layer applied to a substrate region with sealing characteristics according to a third illustrative embodiment of the present invention.

FIG. 15 presents a schematic of the feedthrough region 300 depicting the intermediate layer 240 as applied to two platinum contacts 230. In the embodiment of FIG. 16, where the platinum contacts 320 are electrically active, the sputtering material may be a biocompatible alumina or alumina based glass due to their insulating properties. In other embodiments, in the case of a general hermetic protective layer 270 and a substrate region 210, any suitable biocompatible sputtering material may be employed to form an intermediate layer 240 between the hermetic protective layer 270, which need not be formed of a ceramic material, and the substrate region 210.

With respect to a feedthrough region 300 with a manufacture that requires a lengthy manual assembly process in a clean room environment, the restoration of any breach in the hermetic seal is preferable to the alternative of remanufacturing this component. Similarly, any reinforcement of the hermetic seal may lessen the likelihood of leakage of non biocompatible material contained within housing 121 nor ingress of body fluid into this region which may result in failure of the electrical components.

Referring now to Table 2, there is presented a non exhaustive list of the various combinations of substrates and hermetic protective layers where an intermediate layer may be applied in accordance with the present invention. As an example, a substrate region of gold covered with a hermetic protective layer of ceramic may have its sealing characteristics enhanced by sputtering the gold substrate with either ceramic material or titanium.

TABLE 2

| Substrate | Intermediate Layer | Hermetic Protective Layer |
|---|---|---|
| platinum, iridium, palladium, gold, titanium, ceramic, | ceramic | ceramic |
| platinum, iridium, palladium, gold, titanium, carbon | titanium | ceramic |
| platinum, iridium, palladium, gold, titanium, carbon | titanium | Ceramic and titanium. |

FIG. 16 depicts a substrate region 210 having a protective layer 230 according to a third exemplary embodiment of the present invention. In this embodiment, the depositing of an intermediate layer upon a substrate region 210 which comprises a metal oxide includes a first surface treatment 260 to introduce a layer of sulphur atoms to substantially replace the oxygen atoms in substrate region 210. The surface treated layer 260 is then sputter coated as has been previously described with an intermediate layer 240 such as titanium and then further covered with a protective layer 230 such as silicone or ceramic material as has been previously described.

In an exemplary embodiment, the addition of sulphur onto the biocompatible substrate increases the strength and stability of the bond between the sputtered coating and the underlying sulphur modified substrate region 260. In particular, a metal ion sputtered S-substrate may have an improved interfacial bond due to the known affinity between sulphur and metals.

As will be understood, in an exemplary embodiment of the present invention, strengthening or enhancing the interface bond between the modified substrate region and the hermetic protective layer may provide enhanced sealing characteristics.

As may be inferred from the above, an embodiment of the present invention includes a method of enhancing the bonding characteristics of a protective layer applied to a substrate region of an implantable medical device (IMD) to form a covered substrate region. The method includes depositing an intermediate layer on a portion of the substrate region prior to the application of the protective layer, the intermediate layer binding to the portion of the substrate region to form a modified substrate region having enhanced bonding characteristics with the protective layer. In another embodiment, a system for enhancing the bonding characteristics of a protective layer applied to a substrate region of an implantable medical 30 device (IMD) is provided. The system includes a depositor for depositing an intermediate layer on a portion of the substrate region, the intermediate layer binding to the portion of the substrate region to form a modified substrate region, and a protective layer applicator for applying a protective layer to the substrate region, wherein the protective layer has enhanced bonding characteristics with the modified substrate region. In an exemplary embodiment, the depositor is a sputterer for sputtering the intermediate layer onto the portion of the substrate region.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A method of adhering a protective layer to a substrate region of an implantable medical device (IMD) to form a covered substrate region, comprising:

depositing an intermediate layer on a portion of the substrate region such that the intermediate layer binds to the portion of the substrate region to create a modified substrate region comprising the covered substrate region and a boundary region;

depositing a protective layer onto at least the intermediate layer along the covered substrate region but not along the boundary region; and adhering the protective layer to the intermediate layer along only the covered substrate region such that an increased adhesion exists between the protective layer and the covered substrate region relative to adhesion that would be present between the portion of the substrate region and the protective layer and such that the boundary region improves resistance to delamination at an edge of the covered substrate region.

2. The method of adhering the protective layer as claimed in claim 1, further comprising depositing the intermediate layer by vapor deposition.

3. The method of adhering the protective layer as claimed in claim 1, further comprising depositing the intermediate layer by sputter deposition.

4. The method of adhering the protective layer as claimed in claim 1, wherein the protective layer is a flexible protective layer.

5. The method of adhering the protective layer as claimed in claim 1, wherein the portion of the substrate region includes platinum, wherein the intermediate layer includes titanium, and wherein the protective layer includes silicon.

6. The method of adhering the protective layer as claimed in claim 1, wherein the surface energy of the modified substrate region is higher than the surface energy of the portion of the substrate region, thereby providing the increased adhesion.

7. The method of adhering the protective layer as claimed in claim 5, wherein the stability of the chemical bond between the modified substrate region and the protective layer is increased relative to the stability of the chemical bond that would be present between the portion of the substrate region and the protective layer.

8. The method of adhering the protective layer applied to a substrate region as claimed in claim 4, wherein after application of the protective layer to the substrate region is completed, an exposed substrate region having no protective layer is present, thereby defining a boundary region between the covered substrate region and the exposed substrate region.

9. The method of adhering the protective layer as claimed in claim 1, wherein the protective layer forms a hermetic protective layer between an exterior of the IMD and the portion of the substrate region.

10. The method of adhering the protective layer as claimed in claim 1, wherein the portion of the substrate region includes a mobile oxide layer, wherein the intermediate layer includes a stable oxide component, and wherein the protective layer includes a silicon component.

11. The method of adhering the protective layer as claimed in claim 1, wherein the portion of the substrate region has a surface energy that is substantially lower than the surface energy of the intermediate layer.

12. The method of adhering the protective layer applied to a substrate region as claimed in claim 1, wherein after application of the protective layer to the substrate region is completed, an exposed substrate region having no protective layer is present, thereby defining a boundary region between the covered substrate region and the exposed substrate region.

13. The method of adhering the protective layer applied to a substrate region as claimed in claim 9, wherein the modified substrate region is substantially co-located with the boundary region.

14. The method of adhering the protective layer applied to a substrate region as claimed in claim 1, further including the step of introducing a layer of sulphur atoms to the portion of the substrate region.

15. An implantable medical device (IMD), comprising:
a housing assembly containing electronics components, the housing assembly including a substrate region comprising a modified substrate region that includes a covered substrate region and a boundary region;
an intermediate layer adhering to the substrate region along substantially the entire modified substrate region; and
a protective layer adhering to at least the intermediate layer along the covered substrate region but not along the boundary region such that, at the boundary region, the protective layer is not adhered to the intermediate layer,
wherein an increased adhesion exists between the protective layer and the intermediate layer relative to adhesion that would be present between the substrate region and the protective layer and wherein the boundary region improves resistance to delamination at an edge of the housing assembly.

16. The implantable medical device of claim 15, wherein:
the housing assembly includes a housing having an opening and a metal plate welded to a housing hermetically sealing the opening;
wherein the substrate region is located on at least the metal plate.

17. The implantable medical device of claim 15, wherein the protective layer extends from the substrate region onto the housing.

18. The implantable medical device of claim 16, wherein the plate includes a mobile oxide layer, wherein the intermediate layer includes a stable oxide component, and wherein the protective layer includes a silicon component.

19. The implantable medical device of claim 16, wherein the plate includes platinum, wherein the intermediate layer includes titanium, and wherein the protective layer includes silicon.

20. An implantable medical device (IMD), comprising:
a housing assembly containing electronics components, the housing assembly including a substrate region comprising a modified substrate region that includes a covered substrate region and a boundary region;
an intermediate layer adhering to the substrate region along the modified substrate region; and
a protective layer adhering to at least the intermediate layer such that the protective layer adheres to the intermediate layer along the covered substrate region but does not adhere to the intermediate layer along the boundary region,
wherein a bond between the intermediate layer and the protective layer is a Ti—O—Si bond, and wherein the Ti—O—Si bond is more stable than a PT—O—Si bond
and wherein the boundary region improves resistance to delamination at an edge of the housing assembly.

* * * * *